US00PP11386P

United States Patent [19]

Walden

[11] Patent Number: Plant 11,386

[45] Date of Patent: May 23, 2000

[54] MINIATURE ROSE PLANT NAMED 'JACNIKL'

[75] Inventor: John K. Walden, Thousand Oaks, Calif.

[73] Assignee: Bear Creek Gardens, Inc., Medford, Oreg.

[21] Appl. No.: 09/123,200

[22] Filed: Jul. 27, 1998

[51] Int. Cl.[7] ..... A01H 5/00

[52] U.S. Cl. ..... Plt./121

[58] Field of Search ..... Plt./116, 117, 119, Plt./121

[56] References Cited

U.S. PATENT DOCUMENTS

P.P. 8,031 11/1992 Laver ..... Plt./121

OTHER PUBLICATIONS

UPOV–ROM, 1999/02, GTIJouve Retrieval Software, Plant Variety Database, citation for 'JACnikl'.

*Primary Examiner*—Howard J. Locker

*Attorney, Agent, or Firm*—Klarquist Sparkman Campbell Leigh & Whinston, LLP

[57] ABSTRACT

A miniature rose plant having pale, cream-pink flower color; 1¾ inch open flowers borne singly and in clusters of three to five; pointed ovoid bud form; long flower life on the plant; and medium, dark green, semi-glossy foliage.

1 Drawing Sheet

The present invention relates to a new and distinct variety of rose plant of the miniature class which was originated by me by crossing 'MORsegold', U.S. Plant Pat. No. 6,617, with the variety 'RUImired', U.S. Plant Pat. No. 5,770.

The primary objective of this breeding was to produce a new miniature rose variety having pointed ovoid buds borne in small clusters with 1½ to 2 inch open flowers, long flower life, and suitable for propagation from softwood cuttings and greenhouse production as a miniature pot rose. The objective was substantially achieved, along with other desirable improvements, as evidenced by the following unique combination of characteristics that are outstanding in the new variety and that distinguish it from its parents, as well as from all other varieties of which I am aware:

1. Pale, cream-pink color;
2. 1¾ inch open flowers, borne singly and in clusters;
3. Pointed ovoid bud form;
4. Ten to twelve day flower life, on the plant; and
5. Medium sized, dark green, semi-glossy foliage.

The plant propagates readily from softwood cuttings and is able to be grown in 4-inch pots in a 13–14 week production cycle or in 6-inch pots in a 16–18 week production cycle, making it very capable of pot rose production culture.

Asexual reproduction of this new variety by cuttings, as performed at Somis, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent*.—'MORsegold' (U.S. Plant Pat. No. 6,617).

*Pollen parent*.—'RUImired' (U.S. Plant Pat. No. 5,770).

Classification:

*Botanical*.—Rosa hybrida.

*Commercial*.—Miniature rose.

FLOWER

Observations made January 1994 to July 1998, from specimens grown in a greenhouse environment at Somis, Calif.

Blooming habit: Recurrent

Bud:

*Size*.—About ⅝ inch long when the petals start to unfurl.

*Form*.—The bud form is long, pointed ovoid.

*Color*.—When sepals first divide, bud color is Orange Group 27C. When half blown, the upper and lower sides of the petals are a mixture of Orange Group 27D and Red Group 36D on the outer ⅔ of the petal, with the bottom ⅓ of the petal Yellow Group 2C.

*Sepals*.—Color: Near Green Group 144A. Surface: Slightly rough. There are three very lightly appendaged sepals. There are two unappendaged sepals with hairy edges.

*Receptacles*.—Color: Yellow-Green Group 144A. Shape: Funnel. Size: Small (about 3/16"×¼"). Surface: Smooth.

*Peduncle*.—Length: Short (1⅛"). Surface: Rough, glandular. Color: Green Group 143C. Strength: Erect and slender.

Bloom:

*Size*.—Small. Average open size is 1¾ inches.

*Borne*.—Singly and several together in flat clusters of three to five blooms.

*Stems*.—Normal. Average length is about 4 to 4½ inches.

*Form*.—When first open: High centered. Permanence: Outer petals curl back quill fashion.

*Petalage*.—Number of petals under normal conditions: 40 –45.

*Color*.—The upper sides of the petals are between Red Group 36C and Red Group 36D. The reverse sides of the petals are Red Group 49D on outer ⅔ of petal, changing to Yellow Group 2D on inner ⅓ to petal base. The base of each petal is Yellow Group 3D extending about ¼ inch from petal attachment. The major color on the upper sides is Red Group 36D.

*Variegations*.—None.

*Discoloration*.—At the end of the first day: None, Red Group 36C. At the end of the third day: Near Red Group 36D.

*Fragrance*.—Slight, fruity.

Petals:

*Texture*.—Leathery.

*Shape*.—Oval to deltoid.

*Form*.—Tips slightly recurved.

*Arrangement*.—Imbricated; shingle-like. Petaloids in the center are many, small.

*Persistence*.—Petals hang on and dry.

*Lastingness*.—On the plant: Long (10–12 days). As a cut flower: Not tested.

Reproductive parts:

*Anthers*.—Size: Medium. Quantity: Many. Color: Yellow-Orange Group 22B with reddish tint. Arrangement: Regular around styles.

*Filaments*.—Color: Green-Yellow Group 1C.

*Pollen*.—Yellow-Orange Group 20A.

*Styles*.—Color: Yellow-Green Group 150D.

*Stigmas*.—Color: Greyed-Yellow Group 160B.

Plant:

*Form*.—Bush.

*Growth*.—Vigorous, dwarf, upright, compact.

*Mature plant*.—Height: 14–16 inches. Width: 14 inches.

Foliage: Number of leaflets on normal mid-stem leaves: Five.

*Size*.—Small, (about 3 inches long × 1¾ inches wide).

*Quantity*.—Normal.

*Color*.—New foliage: Upper surface: Between Green Groups 137B and 137C. Lower Surface: Between Yellow-Green Groups 147B and 147C. Old foliage: Upper surface: Near Green Group 137A. Lower surface: Yellow-Green Group 147B.

*Shape*.—Oval.

*Texture*.—Upper side: Smooth.

*Edge*.—Serrated.

*Serration*.—Double.

*Petiole rachis*.—Color: Green Group 137B.

*Petiole underside*.—With prickles.

*Stipules*.—Short (about ⅜ inch long), serrated.

*Disease resistance*.—Tolerant to mildew under normal growing conditions at Somis, Calif. Not tested for blackspot and rust.

Wood:

*New wood*.—Color: Yellow-Green Group 144A. Bark: Smooth.

*Old wood*.—Color: Green Group 137C. Bark: Smooth.

Prickles:

*Quantity*.—On main canes from base: Few. On laterals from main canes: Ordinary.

*Form*.—Short, hooked downward.

*Color when young*.—Red-Purple Group 60B, rapidly changing to Greyed-Orange Group 164B.

*Color when mature*.—Greyed-Orange Group 164B.

Small prickles:

*Quantity*.—On main stalks: None. On laterals: None.

I claim:

1. A novel rose plant of the miniature class as herein shown and described, characterized particularly as to novelty by its pale, cream-pink flower color; 1¾ inch open flowers borne singly and in clusters of three to five; pointed ovoid bud form; long flower life on the plant; and medium, dark green, semi-glossy foliage.

* * * * *

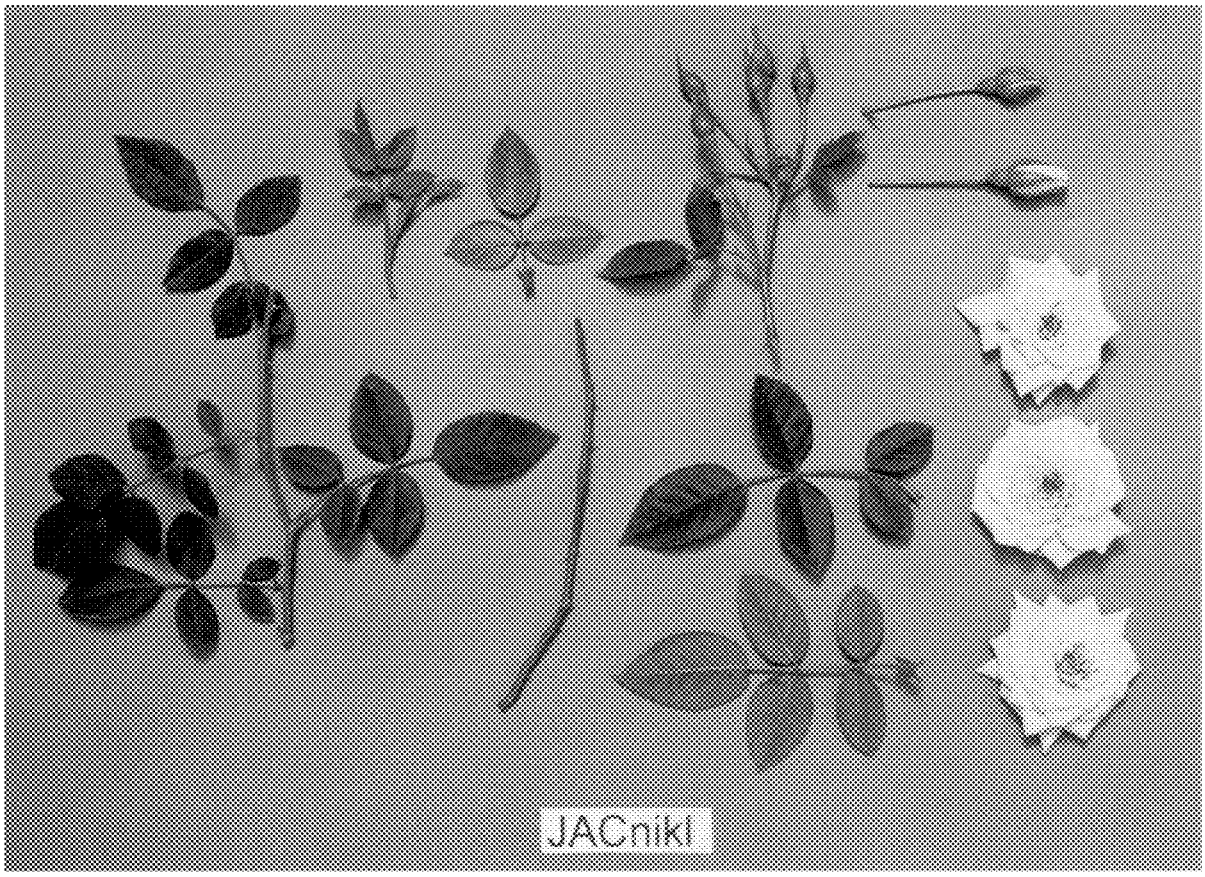
JACniki

UNITED STATES PATENT AND TRADEMARK OFFICE
CERTIFICATE OF CORRECTION

PATENT NO. : PP11,386

DATED : May 23, 2000

INVENTOR(S) : John K. Walden

It is certified that errors appear in the above-identified patent and that said Letters Patent is hereby corrected as shown below:

| Col./Line | Error Reads | Should Read |
|---|---|---|
| 3/9 | None, Red | Red |

Signed and Sealed this

Twenty-ninth Day of May, 2001

*Attest:*

Nicholas P. Godici

NICHOLAS P. GODICI

*Attesting Officer*

*Acting Director of the United States Patent and Trademark Office*